United States Patent [19]

Otte et al.

[11] Patent Number: 4,522,202
[45] Date of Patent: Jun. 11, 1985

[54] CURVED INTRAMEDULLARY LOWER LEG SPIKE

[75] Inventors: Wolf-Dieter Otte; Heinz Otte, both of Volkach, Fed. Rep. of Germany; Siegfried Schider, Reutte, Austria

[73] Assignee: Schwarzkopf Development Corporation, New York, N.Y.

[21] Appl. No.: 566,740

[22] Filed: Dec. 29, 1983

Related U.S. Application Data

[63] Continuation of Ser. No. 338,376, Jan. 11, 1982, abandoned.

[30] Foreign Application Priority Data

Jan. 12, 1981 [AT] Austria ..................................... 72/81

[51] Int. Cl.³ ............................................... A61F 5/46
[52] U.S. Cl. ............................. 128/92 BC; 128/92 C; 3/1; 3/1.9

[58] Field of Search ........... 128/92 B, 92 BA, 92 BC; 3/1, 1.9, 1.91, 1.912, 1.913

[56] References Cited

U.S. PATENT DOCUMENTS 3,441,017  4/1969  Kaessmann ..................... 128/92 BC
4,011,863  3/1977  Zickel ............................ 128/92 BA Primary Examiner—Richard J. Apley
Assistant Examiner—D. J. Isabella
Attorney, Agent, or Firm—Morgan, Finnegan, Pine, Foley & Lee

[57] ABSTRACT

There is disclosed a curved intramedullary lower leg spike in which the face over which cooperates with a driving tool is disposed at an angle with respect to the longitudinal axis of the spike and in which the face area and the front plane of the spike define a divided frontal surface at the leading end of the spike and form an acute angle with the longitudinal axis thereof.

7 Claims, 3 Drawing Figures

CURVED INTRAMEDULLARY LOWER LEG SPIKE

This is a continuation of application Ser. No. 338,376 filed Jan. 11, 1982, now abandoned.

The invention relates to a curved and profilated, single-piece or unitary, intramedullary lower leg spike suitable for being driven into a spike receiving duct in the bone in a direction deviating radically from a normal line extending onto the surface of the bone from the duct, and having on one end of the spike elements for the application of a spike-driving tool.

BACKGROUND OF THE INVENTION

In order to join or connect, or to provide a connecting peg means, in medullated bones, in which the bone marrow spike must be driven into a duct in the bone, outside of the joint area, at an acute angle relative to the longitudinal axis of the bone, as is the case, for example, when joining or connecting bones of the lower leg, use is made, in modern bone surgery, primarily of standardized, slotted, tubular bone marrow spikes, which are curved and provided with a surface profile. One end section of such types of spikes is tapered and serves as guide when driving in the spike. The other end section of such types of spikes has a face perpendicular to the axis of the spike and serves for the application of the tool for driving the spike into the bone. The outer surface area of the spike has a longitudinal profile, which gradually disappears toward the leading end. On the leading end, the spikes generally have a ring-shaped section.

In intramedullary pegging or connecting, it is important for the healing success that the bone marrow spike be anchored in the bone in such a way that it is secure against twisting. Therefore, one important requirement is that the inserted bone marrow spike can find reliable all-around support against the corticalis at the point of insertion, i.e., against the surface of the duct in which the spike is inserted in the bone, with the spike finding sufficient support both on the portion of the surface area which, viewed from the inserted spike, is pointing against the surface of the bone, and against the portion disposed adjacent the inner bone marrow duct. If the spike is additionally provided with a suitable longitudinal surface profile, torsional stability is also reliably assured without totally excluding the possibility of a sliding motion between the spike and the bone and which motion in a longitudinal direction is desirable for the healing success.

Known curved intramedullary spikes with a leading face extending perpendicularly to the axis of the spike have a number of basic drawbacks if inserted into a duct extending in an inclined direction with respect to the surface of the bone. If they are driven only to a depth sufficient to still assure reliable support of the leading end against the corticalis of the total overall spike-receiving duct in the bone, the end of the spike necessarily projects beyond the surface of the bone and comes into contact with the connective tissue covering the bone. This results in pain, tissue infection and similar complications for the patient. On the other hand, if the spike is driven into the bone to a depth sufficient to prevent it from projecting from the surface of the bone, its contact area with the surface of the spike-receiving duct facing the medullary canal is insufficient to reliably assure torsional stability as a result of its surface profile, if any such stability is still available at all, within the end zone of the spike. In such unfavorable cases, the spike may even break through the corticalis into the medullary canal. Consequently, when the above conditions exist, the spike has no torsional stability at all and fails to provide the fixation of the fractured bone parts which is required for healing. Furthermore, a medullary spike, once completely inserted in the medullary canal, is difficult to extract and causes a severe bone defect.

Intramedullary spikes which are provided on their leading ends with an internal thread into which a striking sleeve is screwed are known and they can be driven into the spike-receiving duct in the bone without direct hammering on a face area. However, such spikes generally have an area perpendicular to the axis of the spike on the face side and are, furthermore, normally not provided with a profilated or shaped or curved surface area on the inserted end. Consequently, the drawbacks outlined above apply also to spikes such as these when they are inserted in a spike-receiving duct extending into the bone at an inclination.

In addition, spikes are known which have their leading ends shaped approximately in the form of a round head. The above-mentioned drawbacks also apply to spikes of this type, though to a lesser extent.

An intramedullary two-part spike with rotational stability is disclosed in British Pat. No. 817,525. This spike, once fixed in the bone, has a leading end with a divided face area due to the different depths to which the individual parts of the spike are driven into the bone. Since the two parts of the spike are inserted one after the other, the driving tool cooperates not with said divided surface, but in each case only with the nondivided surface of each individual part of the spike. The projection of larger portions of the spike from the surface of the bone is practically unavoidable with this design of intramedullary spike.

It is the object of the present invention to eliminate the above shortcomings of intramedullary lower leg spikes which are to be driven into a spike-receiving duct in the bone in a direction radically deviating from the vertical line. It is a further object of the invention to provide intramedullary lower leg spikes which rest within the zone of insertion on the total bone tissue with torsional stability all-around, without projecting from the surface of the bone and without causing the aforementioned complications for the patient.

BRIEF STATEMENT OF THE INVENTION

In accordance with the invention, there is provided a curved, unitary intramedullary lower leg spike suitable for being driven into a spike-receiving duct in the bone in a direction radically deviating from a normal line extending onto the surface of the bone from said duct, said spike comprising a longitudinal portion extending up to a striking end, said striking end being provided with a structured face area including elements for applying a driving tool to said striking end and a line drawn in a plane of said structural face area and intersecting the front planar surface of said spike forming an acute angle $\alpha$ with the longitudinal axis of said spike and defining a limited portion of said structural face area with respect to said longitudinal axis.

THE DRAWINGS

Serving to illustrate exemplary embodiments of the present invention are the accompanying drawings which are to be taken in conjunction with the following description of the invention and wherein.

DESCRIPTION OF THE PREFERRED EMBODIMENTS

In a preferred embodiment, the face area on the leading end of the intramedullary lower-leg spike according to the invention is provided with a stepped shape, whereby at least one partial area is aligned perpendicularly to the axis of the spike.

In another preferred embodiment according to the invention, the intramedullary lower leg spike has a slot-shaped recess in the direction of the longitudinal axis of the spike, said recess starting at the face area.

In yet another preferred embodiment of the invention, the face area viewed from the front side has a profilated annular shape with approximately constant wall thickness.

Figure 1:
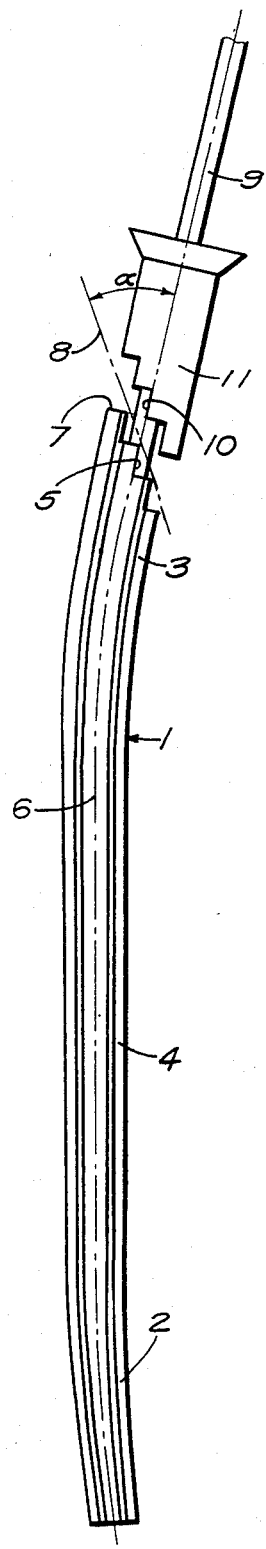
FIG. 1 is a lateral view of a lower leg spike in accordance with the invention showing a stepped structural striking surface and, as well, a portion of a driving or sriking tool adapted to be used therewith.

Referring now to FIG. 1, there is shown there a tubular, curved, intramedullary lower leg spike 1 made of a material and with a profilated or profilar or shaped surface in accordance with EP-Al 0 008 758, the profiling assuring good stability against twisting. The short sections on the tapered ends 2 and 3 of the bone spike are slightly angled against the comparatively long center portion 4. The limiting plane 8 of the structured face area 5 on end 3 of the spike and the longitudinal axis 6 of the spike form an acute angle α, with the inclination being selected in such a way that when the bone spike is completely inserted in a spike-receiving duct of a bone, the limiting plane 8 extends substantially flush with the surface of the bone. The face area 5 has a stepped shape with partial areas 7 disposed perpendicular to the longitudinal axis 6 of the spike. The bone spike is driven into the bone, for example, with the help of the driving tool shown in the figure. The guide part 9 of the tool is screwed into the end of the medullary spike. A driving sleeve 11 is placed over the guide part; the end area 10 of said sleeve being adapted to the face area 5 of the intramedullary spike. The striking hammer may be, for example, a heavy striking barrel which is disposed slidingly over the guide part 9.

Figure 2:
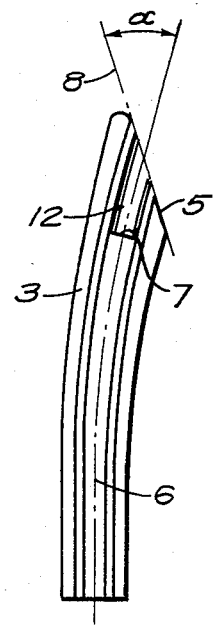
FIG. 2 is a partial lateral view of the spike shown in FIG. 1 provided with a slotted contact surface in the leading end of the spike.

Turning next to FIG. 2, there is illustrated there a lateral view of spike end 3, in which the face area 5 is provided with or subdivided by a slot-like recess 12. The partial area 7 of the recess extends perpendicularly to the longitudinal axis 6 of the spike.

Figure 3:
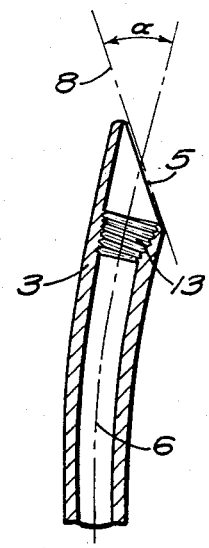
FIG. 3 is a partial, lateral, sectional view of a lower leg spike in accordance with the invention showing the leading end provided with an internal thread.

Now referring to FIG. 3, there is illustrated there the striking portion of another embodiment of a bone spike according to the invention. The bone spike has a tubular shape and is provided with an internal thread 13 in the portion of the spike adjacent face area 5 and towards the center of the spike. In the embodiment shown, the thread is conical in shape and tapered towards the center of the spike. In order to drive the spike, a striking sleeve having suitable matching threads on one end and a striking area extending vertically to the longitudinal axis of the spike on its opposite end is screwed into internal thread 13.

The common feature of all of illustrated spike embodiments is that when driven into an inclined spike-receiving duct in the bone, the spikes will rest with the profilated surface all-around and thus with torsional stability against the corticalis without projecting from the surface of the bone. This advantage has no negative bearing on the handling of the spike. In particular it has no negative effect on the insertion or extraction of the spike into and from the bone. Moreover, a spike in accordance with the invention prevents complications such as those mentioned above in patients in which it is employed. Numerous other advantages of intramedullary spikes according to the invention will be readily apparent to those skilled in the art.

Many variations of the embodiments of this invention may be made without departing from the spirit and scope thereof. It is to be understood, therefore, that this invention is not to be limited to the disclosed embodiments thereof, except as defined in the appended claims.

What is claimed is:

1. A curved, unitary intramedullary, lower leg spike suitable for being driven laterally at an acute angle with respect to the longitudinal axis of a bone, into a spike-receiving duct in said bone, said spike comprising a longitudinal portion, a curved portion, a striking end, and a shaped outer surface which extends along said longitudinal portion up to said striking end, said shaped outer surface being adapted to provide stability against twisting, said striking end having structured elements for actively engaging a driving tool to said spike, and further defining an exposed face area wherein a line drawn in a plane which lies across said face area and which intersects the front planar surface of said spike forms an acute angle with the longitudinal axis of said spike at said striking end, said spike being adapted to contact corticalis along said outer surface up to said striking end.

2. A curved, unitary, intramedullary lower leg spike according to claim 1 wherein the striking end is segmented and at that part thereof is perpendicular to the longitudinal axis of said spike.

3. A curved, unitary, intramedullary lower leg spike according to claim 2 wherein a surface of the striking end is a plurality of steps.

4. A curved, unitary, lower leg spike according to claim 1 wherein the striking end has a slot-shaped recess commencing at the face area which extends downwardly in the direction of the longitudinal axis of said spike.

5. A curved, unitary, intramedullary lower leg spike according to claim 1 wherein the striking end, viewed in a longitudinal direction, has an annular-shaped profile and walls of substantially uniform thickness.

6. A curved, unitary, intramedullary lower leg spike according to claim 1, wherein said striking end is segmented.

7. A curved, unitary, intramedullary lower leg spike according to claim 1 wherein said spike is adapted to be driven into a bone laterally at an acute angle with respect to the longitudinal axis of said bone into a spike-receiving duct in said bone in a direction radically deviating from a normal line extending onto the surface of said bone from said spike-receiving duct.

* * * * *